(12) United States Patent
Al-Ali et al.

(10) Patent No.: US 8,414,499 B2
(45) Date of Patent: Apr. 9, 2013

(54) PLETHYSMOGRAPH VARIABILITY PROCESSOR

(75) Inventors: Ammar Al-Ali, Tustin, CA (US);
Walter Weber, Laguna Hills, CA (US);
Anmol Majmudar, Irvine, CA (US)

(73) Assignee: Masimo Corporation, Irvine, CA (US)

( * ) Notice: Subject to any disclaimer, the term of this patent is extended or adjusted under 35 U.S.C. 154(b) by 1470 days.

(21) Appl. No.: 11/952,940

(22) Filed: Dec. 7, 2007

(65) Prior Publication Data

US 2008/0188760 A1    Aug. 7, 2008

Related U.S. Application Data

(60) Provisional application No. 60/873,663, filed on Dec. 9, 2006, provisional application No. 60/998,782, filed on Oct. 12, 2007.

(51) Int. Cl.
*A61B 5/00* (2006.01)
*A61B 5/02* (2006.01)

(52) U.S. Cl.
USPC .......................................... 600/504; 600/324

(58) Field of Classification Search .................. 600/323, 600/324
See application file for complete search history.

(56) References Cited

U.S. PATENT DOCUMENTS

| | | | |
|---|---|---|---|
| 4,432,374 A | 2/1984 | Osanai | |
| 4,867,165 A * | 9/1989 | Noller et al. | 600/328 |
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |
| 5,163,438 A | 11/1992 | Gordon et al. | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| D359,546 S | 6/1995 | Savage et al. | |
| 5,431,170 A | 7/1995 | Mathews | |

(Continued)

FOREIGN PATENT DOCUMENTS

| | | |
|---|---|---|
| JP | 2001-321347 A | 11/2001 |
| JP | 2002-028138 A | 1/2002 |

(Continued)

OTHER PUBLICATIONS

Cannesson et al., Relation between Respiratory Variations in Pulse Oximetry Plethysmographic Waveform Amplitude and Arterial Pulse Pressure in Ventilated Patients: Critical Care, Aug. 23, 2005; 9(5): 562-568.*

(Continued)

*Primary Examiner* — Navin Natnithithadha
*Assistant Examiner* — Michael R Bloch
(74) *Attorney, Agent, or Firm* — Knobbe Martens Olson & Bear LLP

(57) ABSTRACT

A plethysmograph variability processor inputs a plethysmograph waveform having pulses corresponding to pulsatile blood flow within a tissue site. The processor derives plethysmograph values based upon selected plethysmograph features, determines variability values, and calculates a plethysmograph variability parameter. The variability values indicate the variability of the plethysmograph features. The plethysmograph variability parameter is representative of the variability values and provides a useful indication of various physiological conditions and the efficacy of treatment for those conditions.

29 Claims, 4 Drawing Sheets

U.S. PATENT DOCUMENTS

| | | | |
|---|---|---|---|
| D361,840 S | 8/1995 | Savage et al. | |
| D362,063 S | 9/1995 | Savage et al. | |
| 5,452,717 A | 9/1995 | Branigan et al. | |
| D363,120 S | 10/1995 | Savage et al. | |
| 5,456,252 A | 10/1995 | Vari et al. | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,561,275 A | 10/1996 | Savage et al. | |
| 5,562,002 A | 10/1996 | Lalin | |
| 5,590,649 A | 1/1997 | Caro et al. | |
| 5,602,924 A | 2/1997 | Durand et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,823,950 A | 10/1998 | Diab et al. | |
| 5,830,131 A | 11/1998 | Caro et al. | |
| 5,833,618 A | 11/1998 | Caro et al. | |
| 5,860,919 A | 1/1999 | Kiani-Azarbayjany et al. | |
| 5,890,929 A | 4/1999 | Mills et al. | |
| 5,904,654 A | 5/1999 | Wohltmann et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,027,452 A | 2/2000 | Flaherty et al. | |
| 6,036,642 A | 3/2000 | Diab et al. | |
| 6,045,509 A | 4/2000 | Caro et al. | |
| 6,067,462 A | 5/2000 | Diab et al. | |
| 6,081,735 A | 6/2000 | Diab et al. | |
| 6,088,607 A | 7/2000 | Diab et al. | |
| 6,110,522 A | 8/2000 | Lepper, Jr. et al. | |
| 6,124,597 A | 9/2000 | Shehada | |
| 6,129,675 A | 10/2000 | Jay | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,232,609 B1 | 5/2001 | Snyder et al. | |
| 6,236,872 B1 | 5/2001 | Diab et al. | |
| 6,241,683 B1 | 6/2001 | Macklem et al. | |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,321,100 B1 | 11/2001 | Parker | |
| 6,325,761 B1 | 12/2001 | Jay | |
| 6,334,065 B1 | 12/2001 | Al-Ali et al. | |
| 6,343,224 B1 | 1/2002 | Parker | |
| 6,349,228 B1 | 2/2002 | Kiani et al. | |
| 6,360,114 B1 | 3/2002 | Diab et al. | |
| 6,368,283 B1 | 4/2002 | Xu et al. | |
| 6,371,921 B1 | 4/2002 | Caro et al. | |
| 6,377,829 B1 | 4/2002 | Al-Ali | |
| 6,385,471 B1 * | 5/2002 | Mortz | 600/323 |
| 6,388,240 B2 | 5/2002 | Schulz et al. | |
| 6,397,091 B2 | 5/2002 | Diab et al. | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,501,975 B2 | 12/2002 | Diab et al. | |
| 6,505,059 B1 | 1/2003 | Kollias et al. | |
| 6,515,273 B2 | 2/2003 | Al-Ali | |
| 6,519,487 B1 | 2/2003 | Parker | |
| 6,525,386 B1 | 2/2003 | Mills et al. | |
| 6,526,300 B1 | 2/2003 | Kiani et al. | |
| 6,541,756 B2 | 4/2003 | Schulz et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,595,316 B2 | 7/2003 | Cybulski et al. | |
| 6,597,932 B2 | 7/2003 | Tian et al. | |
| 6,597,933 B2 | 7/2003 | Kiani et al. | |
| 6,606,511 B1 | 8/2003 | Ali et al. | |
| 6,632,181 B2 | 10/2003 | Flaherty et al. | |
| 6,639,668 B1 | 10/2003 | Trepagnier | |
| 6,640,116 B2 | 10/2003 | Diab | |
| 6,643,530 B2 | 11/2003 | Diab et al. | |
| 6,650,917 B2 | 11/2003 | Diab et al. | |
| 6,654,624 B2 | 11/2003 | Diab et al. | |
| 6,658,276 B2 | 12/2003 | Kianl et al. | |
| 6,661,161 B1 | 12/2003 | Lanzo et al. | |
| 6,671,531 B2 | 12/2003 | Al-Ali et al. | |
| 6,678,543 B2 | 1/2004 | Diab et al. | |
| 6,684,090 B2 | 1/2004 | Ali et al. | |
| 6,684,091 B2 | 1/2004 | Parker | |
| 6,697,656 B1 | 2/2004 | Al-Ali | |
| 6,697,657 B1 | 2/2004 | Shehada et al. | |
| 6,697,658 B2 | 2/2004 | Al-Ali | |
| RE38,476 E | 3/2004 | Diab et al. | |
| 6,699,194 B1 | 3/2004 | Diab et al. | |
| 6,714,804 B2 | 3/2004 | Al-Ali et al. | |
| RE38,492 E | 4/2004 | Diab et al. | |
| 6,721,582 B2 | 4/2004 | Trepagnier et al. | |
| 6,721,585 B1 | 4/2004 | Parker | |
| 6,725,075 B2 | 4/2004 | Al-Ali | |
| 6,728,560 B2 | 4/2004 | Kollias et al. | |
| 6,735,459 B2 | 5/2004 | Parker | |
| 6,745,060 B2 | 6/2004 | Diab et al. | |
| 6,760,607 B2 | 7/2004 | Al-Ali | |
| 6,770,028 B1 | 8/2004 | Ali et al. | |
| 6,771,994 B2 | 8/2004 | Kiani et al. | |
| 6,792,300 B1 | 9/2004 | Diab et al. | |
| 6,813,511 B2 | 11/2004 | Diab et al. | |
| 6,816,741 B2 | 11/2004 | Diab | |
| 6,822,564 B2 | 11/2004 | Al-Ali | |
| 6,826,419 B2 | 11/2004 | Diab et al. | |
| 6,830,711 B2 | 12/2004 | Mills et al. | |
| 6,850,787 B2 | 2/2005 | Weber et al. | |
| 6,850,788 B2 | 2/2005 | Al-Ali | |
| 6,852,083 B2 | 2/2005 | Caro et al. | |
| 6,861,639 B2 | 3/2005 | Al-Ali | |
| 6,869,402 B2 | 3/2005 | Arnold | |
| 6,898,452 B2 | 5/2005 | Al-Ali et al. | |
| 6,920,345 B2 | 7/2005 | Al-Ali et al. | |
| 6,931,268 B1 | 8/2005 | Kiani-Azarbayjany et al. | |
| 6,934,570 B2 | 8/2005 | Kiani et al. | |
| 6,939,305 B2 | 9/2005 | Flaherty et al. | |
| 6,942,622 B1 | 9/2005 | Turcott | |
| 6,943,348 B1 | 9/2005 | Coffin, IV | |
| 6,950,687 B2 | 9/2005 | Al-Ali | |
| 6,961,598 B2 | 11/2005 | Diab | |
| 6,970,792 B1 | 11/2005 | Diab | |
| 6,979,812 B2 | 12/2005 | Al-Ali | |
| 6,985,764 B2 | 1/2006 | Mason et al. | |
| 6,993,371 B2 | 1/2006 | Kiani et al. | |
| 6,996,427 B2 | 2/2006 | Ali et al. | |
| 6,999,904 B2 | 2/2006 | Weber et al. | |
| 7,003,338 B2 | 2/2006 | Weber et al. | |
| 7,003,339 B2 | 2/2006 | Diab et al. | |
| 7,015,451 B2 | 3/2006 | Dalke et al. | |
| 7,024,233 B2 | 4/2006 | Ali et al. | |
| 7,027,849 B2 | 4/2006 | Al-Ali | |
| 7,030,749 B2 | 4/2006 | Al-Ali | |
| 7,039,449 B2 | 5/2006 | Al-Ali | |
| 7,041,060 B2 | 5/2006 | Flaherty et al. | |
| 7,044,917 B2 | 5/2006 | Arnold | |

| | | | |
|---|---|---|---|
| 7,044,918 B2 | 5/2006 | Diab | |
| 7,067,893 B2 | 6/2006 | Mills et al. | |
| 7,096,052 B2 | 8/2006 | Mason et al. | |
| 7,096,054 B2 | 8/2006 | Abdul-Hafiz et al. | |
| 7,132,641 B2 | 11/2006 | Schulz et al. | |
| 7,142,901 B2 | 11/2006 | Kiani et al. | |
| 7,149,561 B2 | 12/2006 | Diab | |
| 7,186,966 B2 | 3/2007 | Al-Ali | |
| 7,190,261 B2 | 3/2007 | Al-Ali | |
| 7,215,984 B2 | 5/2007 | Diab | |
| 7,215,986 B2 | 5/2007 | Diab | |
| 7,221,971 B2 | 5/2007 | Diab | |
| 7,225,006 B2 | 5/2007 | Al-Ali et al. | |
| 7,225,007 B2 | 5/2007 | Al-Ali | |
| RE39,672 E | 6/2007 | Shehada et al. | |
| 7,239,905 B2 | 7/2007 | Kiani-Azarbayjany et al. | |
| 7,245,953 B1 | 7/2007 | Parker | |
| 7,254,431 B2 | 8/2007 | Al-Ali | |
| 7,254,433 B2 | 8/2007 | Diab et al. | |
| 7,254,434 B2 | 8/2007 | Schulz et al. | |
| 7,272,425 B2 | 9/2007 | Al-Ali | |
| 7,274,955 B2 | 9/2007 | Kiani et al. | |
| D554,263 S | 10/2007 | Al-Ali | |
| 7,280,858 B2 | 10/2007 | Al-Ali et al. | |
| 7,289,835 B2 | 10/2007 | Mansfield et al. | |
| 7,292,883 B2 | 11/2007 | De Felice et al. | |
| 7,295,866 B2 | 11/2007 | Al-Ali | |
| 7,328,053 B1 | 2/2008 | Diab et al. | |
| 7,332,784 B2 | 2/2008 | Mills et al. | |
| 7,340,287 B2 | 3/2008 | Mason et al. | |
| 7,341,559 B2 | 3/2008 | Schulz et al. | |
| 7,343,186 B2 | 3/2008 | Lamego et al. | |
| D566,282 S | 4/2008 | Al-Ali et al. | |
| 7,355,512 B1 | 4/2008 | Al-Ali | |
| 2005/0085702 A1* | 4/2005 | Diab | 600/324 |
| 2006/0058691 A1 | 3/2006 | Kiani | |
| 2008/0064965 A1* | 3/2008 | Jay et al. | 600/484 |
| 2008/0079299 A1* | 4/2008 | Jackson | 297/284.4 |

FOREIGN PATENT DOCUMENTS

| | | | |
|---|---|---|---|
| JP | 2006-516000 A | | 6/2006 |
| WO | WO 2004/034898 A1 | | 4/2004 |
| WO | WO 2004/080300 A1 | | 9/2004 |
| WO | WO 2005/096922 A1 | | 10/2005 |
| WO | WO 2005096922 A1 | * | 10/2005 |
| WO | WO 2006/097866 | | 9/2006 |

OTHER PUBLICATIONS

Szecsei, Homework Helpers Basic Math and Pre-Algebra, 2006, The Career Press, p. 133.*
Steele DW et al, Continuous Noninvasive Measurement of Pulsus, Academy Emergency Medicine: Official Journal of the Society for Academic emergency Medicine, 1995 , 894-900, 2(10), Hanley & Belfus, Philadelphia, PA.
Dr. James Rayner et al, Continuous Noninvasive Measurement of Pulsus Paradoxus Complements Medical Decision Making in Assessment of Acute Asthma Severity, 2006; 130:754-765.
Gregory D. Jay et al, Analysis of Physician Ability in the Measurement of Pulsus Paradoxus by Sphygmomanometry, 2000; 228;348-352.
Robert F. Tamburro et al, Detection of Pulsus Paradoxus Associated with Large Pericardial Effusions in Pediatric Patients by Analysis of the Pulse-Oximetry Waveform, 2002;109;673-677.
Jeff A. Clark et al, Comparison of Traditional and Plethysmographic Methods for Measuring Pulsus Paradoxus, Jan. 2004; 158:48-51.
Dale W. Steele et al, Pulsus Paradoxus an Objective measure of Severity in Croup, 1998;157:331-334.
Frey B et al, Pulse Oximetry for Assessment of Pulsus Paradoxus: A Clinical Study in Children, Mar. 1999;25(3):333-4.
Steele DW et al, Pulsus Paradoxus: An Objective Measure of Severity in Croup, Nov. 1997;52(11):1115.
Dell R et al, Direct Measurement of Pulsus Paradoxus in Acute Severe Asthma, Sep. 1996;150(9):914-8.
Wright RO et al, Continuous, Noninvasive Measurement of Pulsus Paradoxus in Patients With Acute Asthma, Oct. 1995;2(10):894-900.
Steele DW et al, Continuous Noninvasive Determination of Pulsus Paradoxus: A Pilot Study, Oct. 1995;8(10):1669-74.
Pitson DJ et al, Use of Pulse Transit Time as a Measure of Inspiratory Effort in Patients With Obstructive Sleep Apnoea.
Awad et al., Different Responses of Ear and Finger Pulse Oximeter Wave Form to Cold Pressor Test, Anesth Analg 2001, vol. 92, pp. 1483-1486.
Kirk Shelley M.D., Ph.D., Using the Pulse Oximeter to determine Intravascular Volume Status Non-Invasively, Yale University, School of Medicine, undated PowerPoint presentation, 17 slides.
Shelley et al., What Is the Best Site for Measuring the Effect of Ventilation on the Pulse Oximeter Waveform?, Anesth Analg, Aug. 2006, vol. 103 No. 2, pp. 372-377.
Shelley et al, The Use of Joint Time Frequency Analysis to Quantify the Effect of Ventilation on the Pulse Oximeter Waveform, Journal of Clinical Monitoring and Computing (2006) 20: 81-87.
Cannesson et al., Relation between respiratory variations in pulse oximetry plethysmographic waveform amplitude and arterial pulse pressure in ventilated patients, Critical Care 2005, 9:R562-R568.
Feissel et al., Plethysmographic dynamic indices predict fluid responsiveness in septic ventilated patients, Intensive Care Med (2007) 33, pp. 993-999.
Golparvar et al., Evaluating the Relationship Between Arterial Blood Pressure Changes and Indices of Pulse Oximetric Plethysmography, Anesth Analg 2002 vol. 95, pp. 1686-1690.
Cannesson et al., Respiratory Variations in Pulse Oximetry Plethysmographic Waveform Amplitude to Predict Fluid Responsiveness in the Operating Room, Anesthesiology, V 106, No. 6, Jun. 2007, pp. 1105-1111.
Cannesson et al., Respiratory variations in pulse oximeter waveform amplitude are influenced by venous return in mechanically ventilated patients under general anaesthesia, European Journal of Anaesthesiology 2007, vol. 24, pp. 245-251.
Cannesson et al., New Algorithm for Automatic Estimation of the Respiratory Variations in the Pulse Oxymeter Waveform, ASA Annual Meeting Abstracts Oct. 13, 2007.
Brian L. Partridge, MD, DPhil., Use of Pulse Oximetry as a noninvasive indicator of intravascular volume status, Journal of Clinical Monitoring 1987 vol. 3 No. 4, pp. 263-268.
Shamir et al., Pulse Oximetry plethysmographic waveform during changes in blood volume, British Journal of Anaesthesia 1999 vol. 82 No. 2, pp. 178-181.
Murray et al., The Peripheral Pulse Wave: Information Overlooked, Journal of Clinical Monitoring 1996, vol. 12, pp. 365-377.
Natalini et al., Variations in Arterial Blood Pressure and Photoplethysmography During Mechanical Ventilation, Anesth Analg Nov. 2006 vol. 103 No. 5, pp. 1182-1188.
Natalini et al., Arterial Versus Plethysmographic Dynamic Indices to Test Responsiveness for Testing Fluid Administration in Hypotensive Patients: A Clinical Trial, Anesth Analg Dec. 2006 vol. 103 No. 6, pp. 1478-1484.
Cannesson et al., New Algorithm for Automatic Estimation of the Respiratory Variations in the Pulse Oximeter Waveform in Mechanically Ventilated Patients, Crit Care Med 2007 Abstract vol. 35 No. 12 (Suppl), p. A87.
Cannesson et al., New Algorithm for Automatica Estimation of the Respiratory Variations in the Pulse Oximeter Waveform in Spontaneously Breathing Patients, Crit Care Med 2007 Abstract vol. 35 No. 12 (Suppl), p. A87.
Dorlas, J.C. and J.A. Nijboer (1985) "Photo-electric plethysmography as a monitoring device in anaesthesia. Application and interpretation." British Journal of Anaesthesia 57 (5): 524-30.
James D. and R. Brown (1990). "Vascular volume monitoring with pulse oximetry during pediatric anesthesia [correspondence]." Can J Anaesth 37: 266-7.
Jespersen, L. T. and O. Lederballe (1986). "Quantitative photoplethysmography." Surgery 99(1): 130.
Jespersen, L.T. and O.L. Pedersen (1986). "The quantitative aspect of photoplethysmography revised." Heart Vessels 2(3): 186-90.
Kim, J. M., K. Arakawa, et al (1986). "Pulse oximetry and circulatory kinetics associated with pulse volume amplitude measured by photoelectric plethysmography." Anesth Analg 65 (12): 1333-9.

Lherm. T., T. Chevalier, et al. (1995). "Correlation between plethysmography curve variation (dpleth) and pulmonary capillary wedge pressure (pcwp) in mechanically ventilated patients." British Journal of Anaesthesia Suppl. 1 (74): 41.

Mooser V, Regamey C, Stauffer "Le pouls paradoxal" Schweiz. Rundschau Med. (PRAXIS) 83, Nr. 6 (1994) : pp. 158-162 (with English Abstract).

Maxime Cannesson, MD. "Use of the Pulse Oximeter Waveform as a Non Invasive Functional Hemodynamic Monitoring". Claude Bernard University, Louis Pradel Hospital, undated Power Point presentation in 44 slides.

Paul Barach, MD. "Pulsus Paradoxus". *Hospital Physician*, Jan. 2000, pp. 49-50.

Shelley, et al., Pulse Oximeter Waveform: Photoelectric Plethysmography, in Clinical Monitoring, Carol Lake, R. Hines, and C. Blitt, Eds.: W.B. Saunders Company, 2001, pp. 420-428.

Shelley, et al., Arterial—Pulse Oximetry Loops: A New Method of Monitoring Vascular Tone, Journal of Clinical Monitoring, Jul. 1997, pp. 223-228.

Awad, et al., How Does the Plethysmogram Derived from the Pulse Oximeter Relate to Arterial Blood Pressure in Coronary Artery Bypass Graft Patients?, The International Anesthesia Research Society, 2001, pp. 1466-1471.

Translation of Japanese Office Action in JP App. No. 2009-540509, dated Aug. 23, 2012, 3 pgs.

* cited by examiner

PLETHYSMOGRAPH VARIABILITY PROCESSOR

PRIORITY APPLICATIONS

This application claims priority to prior U.S. Provisional Patent Application No. 60/873,663 filed Dec. 9, 2006 titled Plethysmograph Variability Index and U.S. Provisional Patent Application No. 60/998,782 filed Oct. 12, 2007 titled Plethysmograph Variability Index. All of the above-referenced applications incorporated by reference herein.

BACKGROUND OF THE INVENTION

Pulse oximetry utilizes a noninvasive sensor to measure oxygen saturation ($SpO_2$) and pulse rate of a person. The sensor has light emitting diodes (LEDs) that transmit optical radiation of red and infrared wavelengths into a tissue site and a detector that responds to the intensity of the optical radiation after attenuation by pulsatile arterial blood flowing within the tissue site. Furthermore, the sensor may be attached to a patient's finger, foot, ear lobe, digit or other portion of the body where blood flows close to the skin. Pulse oximeters have gained rapid acceptance in a wide variety of medical applications, including surgical wards, intensive care and neonatal units, general wards, home care, physical training, and virtually all type of monitoring scenarios.

Pulse oximeters capable of reading through motion induced noise are disclosed in at least U.S. Pat. Nos. 6,770,028, 6,658,276, 6,584,336, 6,263,222, 6,157,850, 5,769,785, and 5,632,272, which are assigned to Masimo Corporation ("Masimo") of Irvine, Calif. and are incorporated by reference herein. Low noise pulse oximetry sensors are disclosed in one or more of U.S. Pat. Nos. 7,027,849, 6,985,764, 6,934,570 6,760,607 6,377,829 6,285,896 5,782,757 5,638,818, which are also assigned to Masimo and incorporated by reference herein. Moreover, pulse oximeters capable of reading through motion induced noise and low noise optical sensors including LNOP® disposable, reusable and/or multi-site sensors and Radical®, Rad-5™, Rad-8™, Rad-9™, PPO+™ monitors are also available from Masimo.

Multiple parameter monitors and multiple wavelength sensors are described in U.S. patent application Ser. No. 11/367,033 entitled Noninvasive Multiple Parameter Patient Monitor filed Mar. 1, 2006 and U.S. patent application Ser. No. 11/367,013 entitled Multiple Wavelength Sensor Emitters filed Mar. 1, 2006, incorporated by reference herein. Moreover, multiple parameter monitors and multiple wavelength sensors including Rad-57™ and Radical-7™ monitors and Rainbow™ Rainbow™-brand adhesive and reusable sensors are available from Masimo. MS-brand processor boards incorporating SHARC® DSPs from Analog Devices, Inc. are also available from Masimo.

SUMMARY OF THE INVENTION

An aspect of a plethysmograph variability processor inputs a plethysmograph waveform, derives perfusion values, determines variability values, and calculates a plethysmograph (pleth) variability index. The plethysmograph waveform has pulses corresponding to pulsatile blood flow within a tissue site. The perfusion values correspond to the pulses. The variability values are each indicative of the variability of a series of the perfusion values. The plethysmograph variability index is representative of the variability values. The plethysmograph variability index is displayed.

In various embodiments, the perfusion values are derived by identifying peaks and valleys for the pulses, calculating AC values for the pulses from the peaks and the valleys, calculating DC values for the pulses, and normalizing the AC values with the DC values. Variability values are determined by accumulating the perfusion values in buffers and calculating one of the variability values for each of the buffers. As an example, variability values are determined by sorting the perfusion values within each of the buffers from the largest of the perfusion values to the smallest of the perfusion values and trimming at least one of the largest perfusion values and at least one of the smallest perfusion values from each of the buffers.

Plethysmograph variability indexes (PVIs) are determined from a percentage difference between a maximum perfusion value and a minimum perfusion value for each of the buffers. A median value of the PVIs is calculated. In an embodiment, physiologically acceptable pulses are identified and a minimum amount of time's worth of acceptable data for each buffer is determined. An IR channel is input for the plethysmograph waveform and a red channel is used to verify acceptable pulses.

An aspect of a plethysmograph variability processing system is an optical sensor that transmits multiple wavelengths of optical radiation into a tissue site, detects the optical radiation after attenuation by pulsatile blood flowing within the tissue site, and generates a sensor signal responsive to the detected optical radiation. A patient monitor demodulates the sensor signal so as to generate a plethysmograph channels. A digital signal processor (DSP) within the patient monitor inputs at least one of the plethysmograph channels and outputs a plethysmograph variability (PV) parameter accordingly. A PV process executes on the DSP so as to process the plethysmograph channel and derive the PV parameter. A patient monitor output is responsive to the PV parameter.

In various embodiments, the PV process has a plethysmograph input corresponding to the at least one plethysmograph channel. The pleth has pleth features. A measure pleth process extracts the pleth values from the plethysmograph according to the pleth features. A pleth value input corresponds to the pleth values. A pleth variability process generates a plurality of variability values from the pleth values. A pleth variability input corresponds to the variability values. A variability parameter process generates a pleth variability (PV) parameter from the variability values. Physiological acceptability criteria are applied to the plethysmograph input. A reduce data dispersion process trims outlying ones of the pleth values according to dispersion criteria. Post processing applies at least one of a smoothing or slew rate limit to the PV parameter. Pre-processing applies a bandpass filter to the plethysmograph input so as to remove a cyclical baseline shift or oscillation from the plethysmograph. The patient monitor output generates a graph of the PV parameter versus time so as to indicate a trend in plethysmograph variability.

An aspect of a plethysmograph variability method inputs plethysmograph channels, measures pleth values from the input and defines windows each encompassing a unique time interval of the plethysmograph values. Variability values are calculated, where each of the variability values are derived from the plethysmograph values encompassed in a unique one of the windows. Second windows are defined, each encompassing a unique time interval of the variability values. Parameter values are calculated, where each of the parameter values are derived from the variability values encompassed in a unique one of the second windows. Parameter values are output. In various embodiments, the plethysmograph channels each have pulses corresponding to pulsatile blood flow within a tissue site, and the plethysmograph values are based upon the pulses. The plethysmograph values are measures of blood perfusion at the tissue site. In alternative embodiments, plethysmograph values are based upon area under absorption pulses, an envelope of the pulses, a time series of normalized envelope heights or a time series of normalized envelope areas.

An aspect of a plethysmograph variability processing system has a sensor that transmits multiple wavelengths of optical radiation into a tissue site and that detects the optical radiation after attenuation by pulsatile blood flow within a tissue site so as to provide a plethysmograph input to a digital signal processor (DSP). The input is selected from channels corresponding to the multiple wavelengths. The DSP executes instructions for deriving plethysmograph variability from the plethysmograph. A measuring means generates plethysmograph values from the plethysmograph input according to predefined plethysmograph features. A calculation means derives variability values from the plethysmograph values, and a reduction means deriving a plethysmograph variability (PV) parameter from the plethysmograph values. In various embodiments, a first accumulation means applies a variability formula to a window of plethysmograph values. A dispersion reduction means trims outlying values from the first accumulation means. A second accumulation means applies data reduction criteria to a window of variability values. An acceptance means eliminates pulses from the plethysmograph input that are not physiologically acceptable. A post-processing means limits the slope of the PV parameter.

DETAILED DESCRIPTION OF THE PREFERRED EMBODIMENTS

PV Monitor

Figure 1:
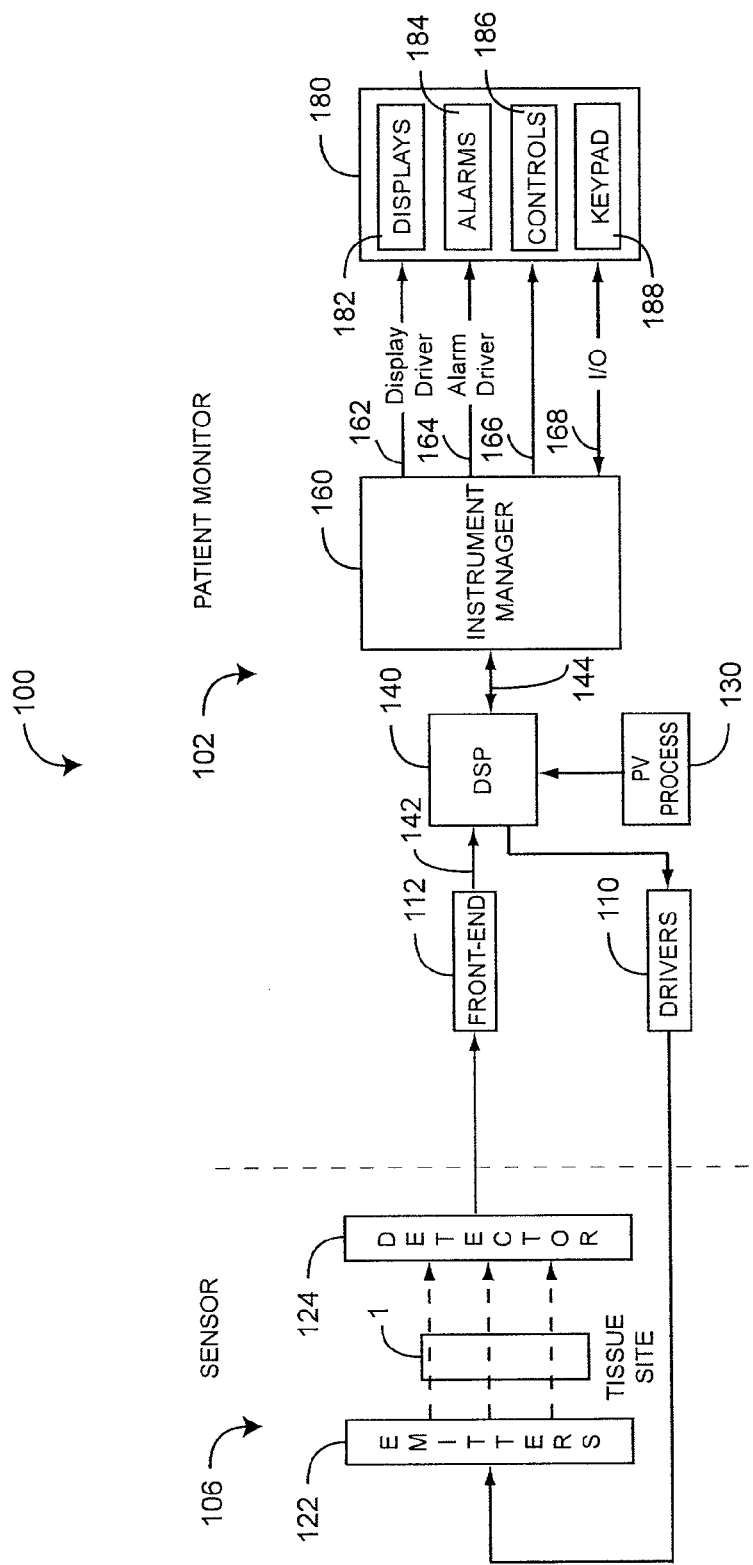
FIG. 1 is a general block diagram of a plethysmograph variability processing system.

FIG. 1 illustrates a plethysmograph variability processing system 100 embodiment, which calculates one or more measures of plethysmograph variability (PV). The plethysmograph variability processing system 100 advantageously provides at least some of displays, alarms or controls responsive to PV so as to indicate, and affect the treatment of, a patient condition. The PV processing system 100 may further generate SpO$_2$, pulse rate (PR), perfusion index (PI), signal quality and in multiple wavelength configurations additional blood parameter measurements such as HbCO and HbMet.

As shown in FIG. 1, the PV processing system 100 has a patient monitor 102 and a sensor 106. The sensor 106 attaches to a tissue site 1 and includes a plurality of emitters 122 capable of irradiating the tissue site 1 with at least two wavelengths of light, such as the red and infrared (IR) wavelengths utilized in pulse oximeters and in some configurations multiple wavelengths different than or in addition to those red and IR wavelengths. The sensor 106 also includes one or more detectors 124 capable of detecting the light after attenuation by the tissue 1.

Also shown in FIG. 1, the patient monitor 102 communicates with the sensor 106 to receive one or more intensity signals indicative of one or more physiological parameters and displays the parameter values. Drivers 110 convert digital control signals into analog drive signals capable of driving sensor emitters 122. A front-end 112 converts composite analog intensity signal(s) from light sensitive detector(s) 124 into digital data 142 input to the DSP 140. The input digital data 142 is referred to herein as a plethysmograph waveform, plethysmograph or pleth for short. The digital data 142 has plethysmograph channels corresponding to each emitter wavelength, such as a red channel and an IR channel. The digital data 142 is representative of a change in the absorption of particular wavelengths of light as a function of the changes in body tissue resulting from pulsing blood. The DSP 140 may comprise a wide variety of data and/or signal processors capable of executing programs for determining physiological parameters from input data. In an embodiment, the DSP executes one or more pleth variability (PV) processes 130, such as described with respect to FIGS. 3-4, below. In an embodiment, the PV processes 130 may be implemented in software, firmware or other form of code or instructions, or logic or other hardware, or a combination of the above.

Further shown in FIG. 1, the instrument manager 160 may comprise one or more microcontrollers controlling system management, such as monitoring the activity of the DSP 140. One or more output devices 180 include displays 182, alarms 184 and controls 186. Displays 182 may be numerical, such as readouts, or graphical, such as trends and bar graphs, generated by LEDs, LCDs or CRTs to name a few. Displays 182 may also be indicators, such as LEDs of various colors that signify variability magnitude. Alarms 184 may be visual or audible indications that variability is, say, above a predetermined threshold. Controls 186 may be inputs to medical equipment, such as drug administration devices, ventilators and fluid IVs, so as to control the amount of administered drugs, ventilator settings or the amount of infused fluids based up pleth variability. The instrument manager 160 also has an input/output (I/O) port 168 that provides a user and/or device interface for communicating with the monitor 102. User input devices 188 may include a keypad, touch screen, pointing device, voice recognition device, network and computer, to name a few. In an embodiment, the I/O port 168 provides initialization settings for PV processes, as described below. The monitor 102 may also be capable of storing or displaying historical or trending data related to PV and other measured parameters or combinations of measured parameters.

Pleth Waveform

Figure 2:
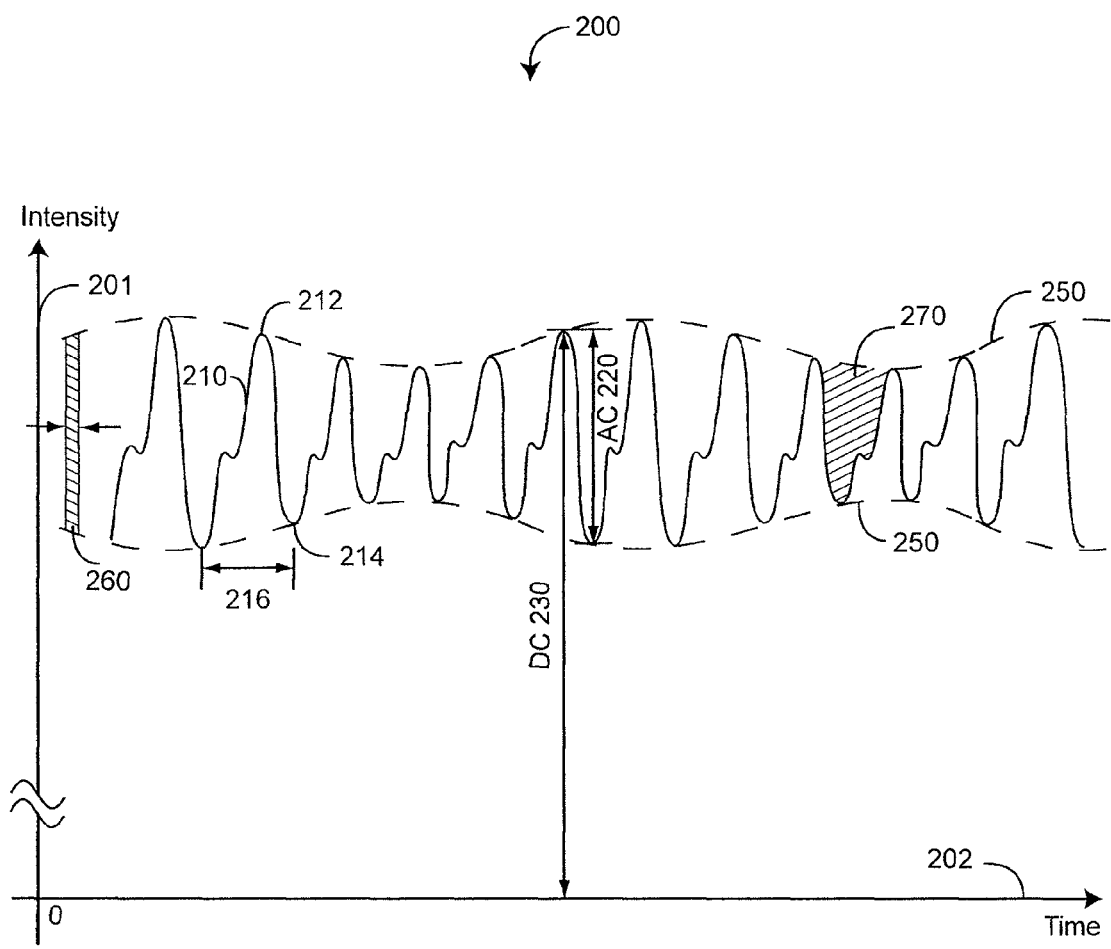
FIG. 2 is a graph of an exemplar plethysmograph.

FIG. 2 illustrates a plethysmograph 200 plotted on an intensity axis 201 versus a time axis 202. The plethysmograph 200 has multiple pulses 210 each with a peak 212 and a valley 214 and extending over a time period 216. A perfusion index (PI) value can be defined for each pulse 210:

$$PI = \frac{AC}{DC} \quad (1)$$

"AC" 220 designates a peak amplitude 212 minus a valley amplitude 214 for a particular pulse. "DC" 230 designates a peak amplitude 212 for a particular pulse. A plethysmograph variability measure is calculated that is responsive to the magnitude of pleth variations, such as depicted by envelope 250. One variability measure is a plethysmograph variability index (PVI), described with respect to FIG. 3, below. Other plethysmograph variability (PV) measures are described with respect to FIG. 4, below. Advantageously, PV measures may provide a numerical indication of a person's physical condition or health.

Pleth Variability Index (PVI)

Figure 3:
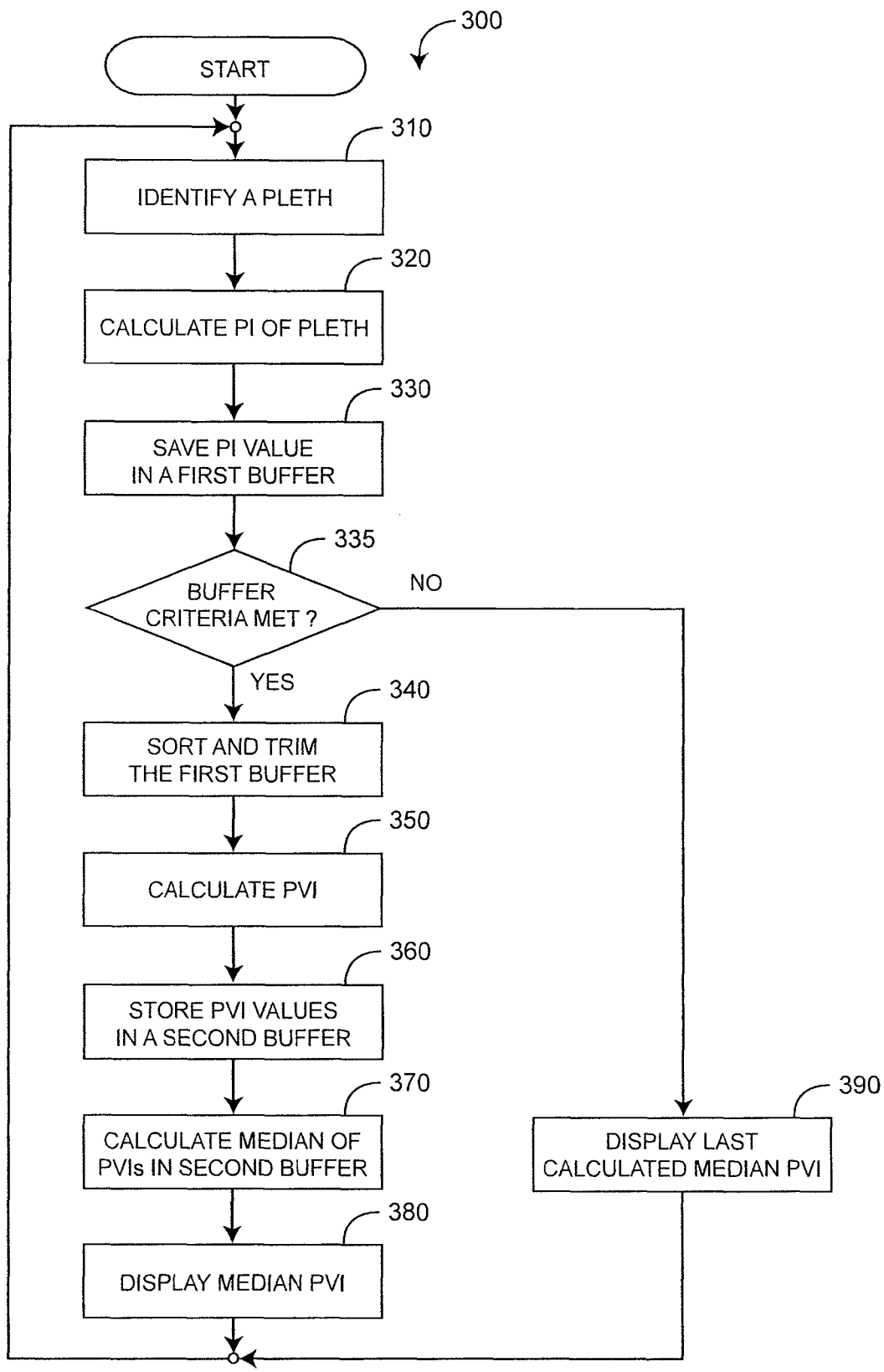
FIG. 3 is a detailed flow chart of a plethysmograph variability index process.

FIG. 3 illustrates a PVI process 300 embodiment, which derives and displays a plethysmograph variability index (PVI). Initially, a first buffer is filled with calculated perfusion index (PI) values 310-330. In an embodiment, these values are based upon the IR channel, as described above. If a sufficient amount of physiologically acceptable data is in the first buffer 335, then a second buffer is filled with calculated plethysmograph variability index (PVI) values 340-360. The median PVI in the second buffer is calculated and displayed 370-380. If the amount of acceptable data in the first buffer is insufficient, then the display is frozen with the last calculated median PVI 390.

As shown in FIG. 3, a plethysmograph is first identified 310. In particular, only physiologically acceptable pulses are used for calculating PI. Physiological plethysmograph identification is disclosed in U.S. Pat. No. 7,044,918 entitled Plethysmograph Pulse Recognition Processor, which is assigned to Masimo and incorporated by reference herein. In an embodiment, the red channel plethysmograph is utilized to verify acceptable pulses in the IR channel. The PI of each acceptable plethysmograph is then calculated 320 according to EQ. 1 and as described with respect to FIG. 2, above. The calculated PIs are stored in a first buffer 330, and the buffer criteria are tested 335. The buffer criteria require both a minimum number of acceptable pulses and a minimum amount of time of acceptable data in the first buffer.

In an embodiment, a plethysmograph 200 (FIG. 2) has a 62.5 Hz sample rate, i.e. a sample interval of 16 msec. The first buffer holds 15 sec. of data at that sample rate. Accordingly, a sliding 15 sec. window of plethysmograph data is stored in the first buffer, and the window is moved in 1.2 sec. increments. The minimum number of acceptable pulses in the first buffer is 6, and the minimum amount of acceptable data in the first buffer is 7.5 sec. The 15 sec. window size allows one respiration cycle, assuming a worse case respiration rate of 4 breaths per min. This window size also allows 6 PIs assuming a worse case pulse rate of 25 bpm. Partial plethysmograph cycles cutoff by a particular window are ignored by that window, but are taken into account in the next window.

Also shown in FIG. 3, if the buffer criteria are met 335, then the first buffer is sorted and trimmed 340. The sort orders the PI values from the minimum PI at one end of the buffer to the maximum PI at the other end of the buffer. Then a predetermined number of PIs are dropped from each end of the buffer, i.e. both the maximum PIs and the minimum PIs are deleted. In an embodiment, 12% of the PIs are trimmed from each end of the buffer. For example, if the buffer holds 10 PIs, a 12% trim=floor(10·12/100)=floor(1.2)=1, where the floor operator truncates digits to the right of the decimal point. Hence, in this example, one max PI and one min PI are dropped from the first buffer. A plethysmograph variability index (PVI) is then calculated 350 from the trimmed first buffer. In an embodiment, PVI is calculated as:

$$PVI = \frac{PI_{MAX} - PI_{MIN}}{PI_{MAX}} \times 100 \quad (2)$$

That is, PVI is the PI variation, expressed as a percentage of the maximum PI, reflected by the PI values remaining in the first buffer.

Further shown in FIG. 3, calculated PVIs are stored in a second buffer 360. In an embodiment, the second buffer holds 11 PVIs, where one PVI is derived for every 1.2 sec shift in the sliding 15 sec. window described above. Next, the median PVI is calculated from the second buffer. This median PVI value is communicated to a display 380. If the buffer criteria 335, described above, are not met, then the last calculated median PVI value is displayed 390. That is, the display is frozen with that last calculated median PVI value until the buffer criteria are satisfied.

In an embodiment, the median PVI value is displayed as a two-digit numerical value on a monitor screen along with other parameters, such as $SpO_2$ and pulse rate. In an embodiment, the median PVI value is displayed on a monitor screen as vertical or horizontal bar graph. In an embodiment, the median PVI value is displayed on a monitor screen as trend graph versus time. In an embodiment, the median PVI value is compared to a predetermined maximum PVI threshold. If the median PVI value crosses the predetermined threshold, one or more visual or audible alarms are triggered. In an embodiment, a visual PVI alarm is one or more colored indicators, such as green, yellow and red, indicating levels of patient health or physiological condition.

Plethysmograph Variability (PV)

Figure 4:
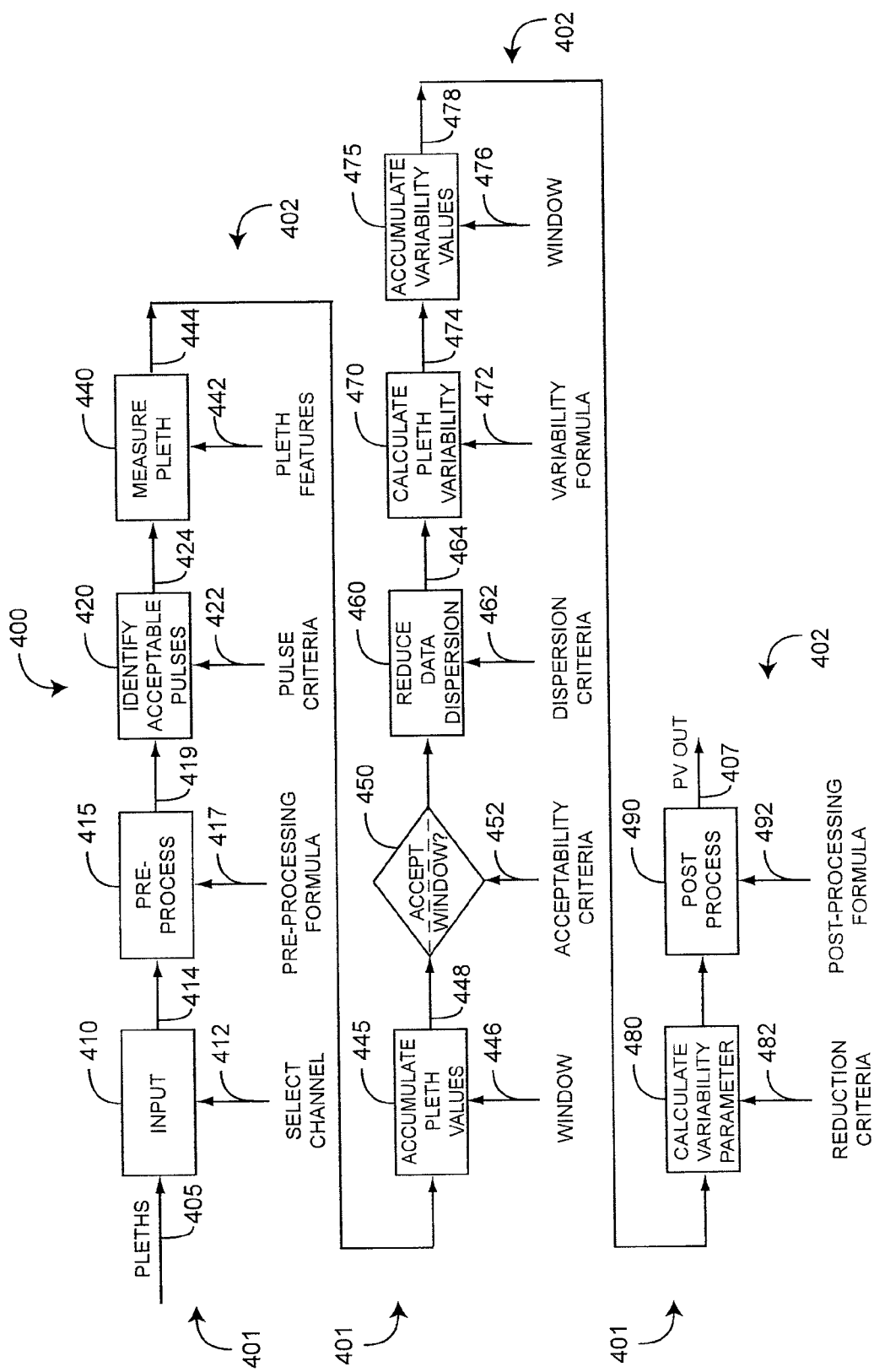
FIG. 4 is a general functional flow diagram of a plethysmograph variability process.

FIG. 4 illustrates a plethysmograph variability (PV) processor 400 embodiment having process steps 401 and initializations 402. The initializations 402 determine the specific characteristics of the process steps 401. The PV processor 400 inputs one or more plethysmograph (pleth) channels 405 and generates PV outputs 407. The pleth channels 405 each correspond to a different optical sensor wavelength, such as a red wavelength channel and an IR wavelength channel corresponding to red and IR emitters of a pulse oximeter sensor. There may be more than two channels when using a multiple wavelength sensor, such as described in U.S. patent application Ser. No. 11/367,013, cited above. For example, there may be eight channels varying in wavelength from about 630 nm to about 905 nm. In an embodiment, two or more pleth channels 405 are processed in parallel or combined as a composite pleth for increased accuracy or robustness in PV calculations. Input 410 determines which pleth channel 405 is used as the pleth input 414 for PV calculations, according to a select channel initialization 412. Input 410 may select any single channel 405 or some combination of channels 405. Pre-process 415 modifies the pleth input 414 according to a predetermined formula 417. In an embodiment, pre-process 415 filters the pleth input 414 so as to remove any slow variation or low frequency oscillation in the plethysmograph baseline or average value, such as a respiration-induced variation that shifts the entire plethysmograph up and down with inhalation and exhalation. In an embodiment, pre-process 415 is a band-pass filter having a 30 to 550 beats per minute passband. Identify acceptable pulses 420 applies pulse criteria 422 to pass only physiologically acceptable pulses 424, such as disclosed in U.S. Pat. No. 7,044,918 cited above.

As shown in FIG. 4, measure pleth 440 extracts pleth values 444 from the remaining pulses 424 according to pleth features 442. The pleth features 434 may be a pulse peak 212 (FIG. 2) and pulse valley 214 (FIG. 2) and the pleth values 444 may relate to perfusion, such as PI described with respect to EQ. 1 above. In another embodiment, the "DC" value in EQ. 1 may be other than a pulse peak, such as a pulse valley or an average of pulse peak and pulse valley, to name a few. In other embodiments, pleth features 442 may include more that two values per pulse and pleth values 444 may be other than perfusion related. Also, measure pleth 440 may be performed over more than one pulse per pleth value 444.

As shown in FIGS. 2 and 4, in an embodiment, pleth features 442 define a pleth envelope 250 interpolated from pulse peaks 212 and pulse valleys 214. Measure pleth 440 defines a series of adjacent slices 260 of envelope height and Δ width, where Δ may vary from one pleth sample to many samples. Accordingly, pleth values 444 are the areas of each slice. In another embodiment, measure pleth 440 calculates the area under each absorption pleth pulse 270, the absorption pleth being the inverse of the intensity pleth 200. In an embodiment, the slices 260 or areas 270 are normalized with respect to a pleth value, such as a DC value or an average value, to name a few.

Also shown in FIG. 4, accumulate pleth values 445 identifies those pleth values 444 within a specified window 446. Accept window 450 determines whether there are a sufficient number of pleth values within the window 446. If not, the remaining steps 460-490 are bypassed and a default PV output 407 is generated. If so, the remaining steps 460-490 are performed. Reduce data dispersion 460 eliminates outlying data, leaving trimmed pleth values 464, according to a dispersion criteria 462. Calculate pleth variability 470 determines a variability value 474 from the trimmed pleth values 464 according to a variability formula 472. In an embodiment, the variability formula is the percentage variability in a window compared with a maximum value in the window, such as described with respect to EQ. 2, above. Accumulate variability values 475 identifies those variability values 474 within a specified window 476. Windows 446, 476 are sliding time intervals or segments having predetermined sizes according to an initialization 402. Adjacent windows may be spaced apart, abutting or overlapping in time.

Further shown in FIG. 4, calculate variability parameter 480 determines a pleth variability (PV) parameter 407 from the accumulated variability values 478 according to a reduction criteria 482. In an embodiment, PV 407 is a median of the variability values 478 in the window 476. In other embodiments, PV 407 is any of average, mode, geometric mean or weighted mean of the windowed variability values, to name a few. Post processing on the PV parameter 407 data may be performed including smoothing and a slew rate filter. In an embodiment, an exponential smoothing is used. The slew rate filter limits the positive or negative slope of the PV parameter 407 to a predetermined maximum.

PV Applications

Many clinicians currently observe a pulse oximeter plethysmograph waveform for changes in patient physiology. Unfortunately, there is no consistency among pulse oximeter manufacturers in the way a plethysmograph waveform is displayed. Further, smoothing, autoscaling and other display data processing mask changes in the raw plethysmograph waveform. Thus, some patient physiology cannot be readily predicted from mere observation of a bedside monitor plethysmograph display. Pleth variability (PV) parameters, such as PVI, advantageously quantify plethysmograph waveform variations, which are displayed in a numerical format that can also be trended as needed. Accordingly, even slight changes in physiology may be reliably observed.

PV can be advantageously used for noninvasive functional hemodynamic monitoring. A plethysmograph waveform is responsive to beat-to-beat changes in peripheral blood volume and perfusion. Thus, plethysmograph variability reflects changes in the intravascular volume status of patients. PV parameters, as described above, are clinically useful hemodynamic measurements that respond to changes in, for example, volemia, fluid responsiveness and ventricular preload. Volemia relates to the volume of blood circulating throughout the body, which is difficult to estimate in a clinical setting. Hypovolemia, for example, is an abnormally low blood volume. Fluid responsiveness is the percent increase in ventricular stroke volume after fluid volume expansion. Ventricular preload is the degree of tension in the cardiac muscle when it begins to contract.

In particularly advantageous embodiments, a PV parameter is monitored during patient treatments. As an example, a downward trend in PV monitored during the addition of fluids to a suspected hypovolemic patient indicates the efficacy of that treatment. Likewise, a downward trend in PV monitored during administration of drugs for asthma indicates the efficacy of the administered drug and the likelihood that the asthma can be controlled.

PVI or other pulse variability (PV) measure may be a significant parameter in a variety of critical conditions, for example those conditions shown in Table 1, below.

TABLE 1

| Conditions Associated with Increased PV | |
|---|---|
| Cardiac Causes | Non-Cardiac Causes |
| Cardiogenic Shock | Hypovolemia |
| Cardiac Tamponade | Septic Shock |
| Pericardial Effusion | Anaphylactic Shock |
| Constrictive Pericarditis | Superior Vena Cava Obstruction |
| Restrictive Cardiomyopathy | Asthma |
| Acute myocardial infarction | |

A plethysmograph variability processor has been disclosed in detail in connection with various embodiments. These embodiments are disclosed by way of examples only and are not to limit the scope of the claims that follow. One of ordinary skill in art will appreciate many variations and modifications.

What is claimed is:
1. A plethysmograph variability method comprising:
inputting a plethysmograph waveform having pulses corresponding to pulsatile blood flow within a tissue site;
deriving a plurality of perfusion values corresponding to the pulses, wherein deriving the plurality of perfusion values comprises:
identifying of the pulses and valleys of the pulses,
calculating differential values for the pulses from the peaks of the pulses and the valleys of the pulses,
determining reference values for the pulses, and
normalizing the differential values with the reference values;
determining a plurality of variability values indicative of the variability of a plurality of series of perfusion values, wherein each variability value is determined by calculating a difference between a first perfusion value of a series of perfusion values and a second perfusion value of the series of perfusion values and normalizing the difference with the first perfusion value;
calculating a plethysmograph variability parameter representative of the plurality of variability values; and
displaying the plethysmograph variability parameter.
2. The plethysmograph variability method according to claim 1, wherein determining variability values comprises:
accumulating the plurality of perfusion values in a plurality of buffers; and
calculating at least one of the plurality of variability values for each of the buffers.

3. The plethysmograph variability method according to claim 2, wherein determining the plurality of variability values further comprises:
sorting the plurality of perfusion values within each of the buffers from a largest perfusion value to a smallest perfusion value; and
trimming at least one perfusion value from a set of largest perfusion values and at least one perfusion value from a set of smallest perfusion values from each of the buffers.

4. The plethysmograph variability method according to claim 3, wherein determining variability values further comprises calculating a plurality of plethysmograph variability indexes (PVIs) from a percentage difference between a maximum perfusion value and a minimum perfusion value for each of the buffers.

5. The plethysmograph variability method according to claim 4, wherein calculating a plethysmograph variability parameter comprises calculating a median value of the PVIs.

6. The plethysmograph variability method according to claim 5, further comprising:
identifying the pulses, wherein the pulses comprise physiologically acceptable pulses identified from a group comprising the physiologically acceptable pulses and physiologically unacceptable pulses; and
determining a minimum amount of time of acceptable data in each of the buffers.

7. The plethysmograph variability method according to claim 6, further comprising:
verifying the physiologically acceptable pulses using a red channel,
wherein inputting the plethysmograph waveform comprises using an IR channel for the plethysmograph waveform.

8. The plethysmograph variability method according to claim 1, wherein the first perfusion value is a largest perfusion value of the series of perfusion values and the second perfusion value is a smallest perfusion value of the series of perfusion values.

9. The plethysmograph variability method according to claim 1, wherein the first perfusion value is a maximum perfusion value of the plurality of perfusion values and the second perfusion value is a minimum perfusion value of the plurality of perfusion values.

10. The plethysmograph variability method according to claim 1, wherein the reference values comprise the peaks of the pulses.

11. The plethysmograph variability method according to claim 1, wherein the reference values comprise the valleys of the pulses.

12. The plethysmograph variability method according to claim 1, wherein the reference values comprise averages of the peaks of the pulses and the valleys of the pulses.

13. A plethysmograph variability processing system comprising:
an optical sensor that transmits multiple wavelengths of optical radiation into a tissue site, detects the optical radiation after attenuation by pulsatile blood flowing within the tissue site, and generates a sensor signal responsive to the detected optical radiation;
a patient monitor that demodulates the sensor signal so as to generate a plurality of plethysmograph channels; and
a digital signal processor (DSP) within the patient monitor configured to:
receive at least one plethysmograph channel of the plurality of plethysmograph channels,
determine a plurality of plethysmograph values from the at least one plethysmograph channel, wherein the plethysmograph values comprise perfusion values that are calculated by normalizing differences between peaks of the at least one plethysmograph channel and valleys of the at least one plethysmograph channel with reference values,
calculate a plurality of variability values based on the plurality of plethysmograph values, wherein each variability value is calculated by normalizing a difference between a first perfusion value and a second perfusion value with the first perfusion value,
calculate a plethysmograph variability (PV) parameter based on the plurality of variability values,
generate a patient monitor output that is responsive to the PV parameter.

14. The plethysmograph variability processing system according to claim 13, wherein the DSP is further configured to apply physiological acceptability criteria to the plethysmograph values.

15. The plethysmograph variability processing system according to claim 14, wherein the DSP is further configured to remove plethysmograph values according to dispersion criteria.

16. The plethysmograph variability processing system according to claim 15, wherein the DSP is further configured to apply at least one of a smoothing or slew rate limit to the PV parameter.

17. The plethysmograph variability processing system according to claim 16, wherein the DSP is further configured to apply a bandpass filter to the at least one plethysmograph channel to remove a cyclical baseline shift.

18. The plethysmograph variability processing system according to claim 17, wherein the patient monitor output generates a graph of the PV parameter versus time so as to indicate a trend in plethysmograph variability.

19. The plethysmograph variability processing system according to claim 13, wherein the optical sensor is associated with one of a foot, an ear, and a digit.

20. The plethysmograph variability processing system according to claim 13, wherein the optical sensor is associated with a body portion wherein blood flows close to the skin.

21. A plethysmograph variability method comprising:
inputting at least one plethysmograph channel of a plurality of plethysmograph channels;
calculating a plurality of plethysmograph values from the at least one plethysmograph channel by normalizing differences between peaks of the at least one plethysmograph channel and valleys of the at least one plethysmograph channel with reference values;
defining a plurality of windows each encompassing a unique time interval of the plethysmograph values;
calculating a plurality of variability values, each of the variability values derived by normalizing a difference between a first plethysmograph value in a first window and a second plethysmograph value in the first window with the first plethysmograph value;
defining a second plurality of windows each encompassing a unique time interval of the variability values;
calculating a plurality of parameter values, each of the parameter values derived from the variability values encompassed in a unique one of the second windows; and
outputting the parameter values.

22. The plethysmograph variability method according to claim 21, wherein:

the plethysmograph channels each have a plurality of pulses corresponding to pulsatile blood flow within a tissue site; and the plethysmograph values are based upon the pulses.

23. A plethysmograph variability processing system having a sensor that transmits multiple wavelengths of optical radiation into a tissue site and that detects the optical radiation after attenuation by pulsatile blood flow within a tissue site so as to provide a plethysmograph input to a digital signal processor (DSP), the input selected from a plurality of channels corresponding to the multiple wavelengths, the DSP executes instructions for deriving plethysmograph variability from the plethysmograph, comprising:

a plethysmograph input;

means for generating plethysmograph values from the plethysmograph input by normalizing differences between peaks of the plethysmograph input and valleys of the plethysmograph input with reference values;

means for deriving variability values from the plethysmograph values, wherein each variability value is determined by calculating a difference between a first plethysmograph value and a second plethysmograph value and normalizing the difference with the first plethysmograph value; and means for deriving a plethysmograph variability (PV) parameter from the plethysmograph values.

24. The plethysmograph variability processing system according to claim 23, further comprising means for removing outlying plethysmograph values.

25. The plethysmograph variability processing system according to claim 24, further comprising means for applying data reduction criteria to a window of variability values.

26. The plethysmograph variability processing system according to claim 25, further comprising means for eliminating pulses from the plethysmograph input that are not physiologically acceptable.

27. The plethysmograph variability processing system according to claim 26, further comprising means for limiting the slope of the PV parameter.

28. The plethysmograph variability processing system according to claim 23, wherein the tissue site is at least a portion of one of a foot, an ear, and a digit.

29. The plethysmograph variability processing system according to claim 23, wherein the tissue site located at or near a body portion where blood flows close to the skin.

* * * * *